(12) United States Patent
Farazi

(10) Patent No.: US 7,697,978 B1
(45) Date of Patent: Apr. 13, 2010

(54) SYSTEMS AND METHODS FOR DETECTING ALTERNANS IN INTRINSIC RHYTHMS TO MONITOR MYOCARDIAL STABILITY

(75) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 642 days.

(21) Appl. No.: 11/561,259

(22) Filed: Nov. 17, 2006

(51) Int. Cl.
*A61B 5/04* (2006.01)
(52) U.S. Cl. .................................... 600/515
(58) Field of Classification Search ................ 600/483, 600/512, 515, 516, 529; 607/4, 5, 9, 14, 607/15, 17; 370/458; 221/14
See application file for complete search history.

(56) References Cited

U.S. PATENT DOCUMENTS

| | | | |
|---|---|---|---|
| 3,658,055 A * | 4/1972 | Abe et al. .................. | 600/516 |
| 5,148,812 A | 9/1992 | Verrier et al. | |
| 6,169,919 B1 | 1/2001 | Nearing et al. | |
| 6,272,377 B1 | 8/2001 | Sweeney et al. | |
| 6,400,982 B2 | 6/2002 | Sweeney et al. | |
| 6,823,213 B1 | 11/2004 | Norris et al. | |
| 7,254,177 B2 * | 8/2007 | Zhou ......................... | 375/257 |
| 2001/0020136 A1 | 9/2001 | Sweeney et al. | |
| 2002/0016550 A1 | 2/2002 | Sweeney et al. | |
| 2004/0002743 A1 | 1/2004 | Park et al. | |
| 2004/0176696 A1 | 9/2004 | Mortara | |
| 2005/0004608 A1 | 1/2005 | Bullinga | |
| 2005/0010124 A1 | 1/2005 | Couderc | |

FOREIGN PATENT DOCUMENTS

WO 0124876 A1 4/2001

* cited by examiner

*Primary Examiner*—George Manuel
*Assistant Examiner*—Robert N Wieland
(74) *Attorney, Agent, or Firm*—Steven M. Mitchell

(57) ABSTRACT

Implantable systems, and methods for use therewith, are provided for monitoring myocardial stability based on a signal that is indicative of functioning of a patient's heart for a plurality of consecutive beats. Sample data is obtained that is representative of functioning of a patient's heart for a plurality of consecutive beats, wherein each beat has a corresponding cycle length that may differ from cycle lengths of other beats. Such sample data is adjusted so that cycle lengths of consecutive beats represented in the adjusted sample data are substantially equal. Myocardial stability is then monitored based on the adjusted sample data. Where the obtained sample data is representative of electrical functioning of the patient's heart, electrical stability can be monitored, e.g., by monitoring for electrical alternations. Where the obtained sample data is representative of mechanical functioning of the patient's heart, mechanical stability can be monitored, e.g., by monitoring for mechanical alternans.

22 Claims, 6 Drawing Sheets

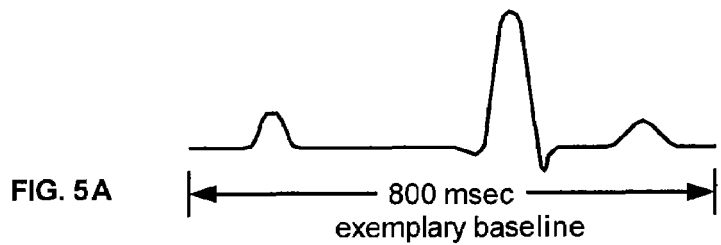
FIG. 5A  |← 800 msec →|
         exemplary baseline
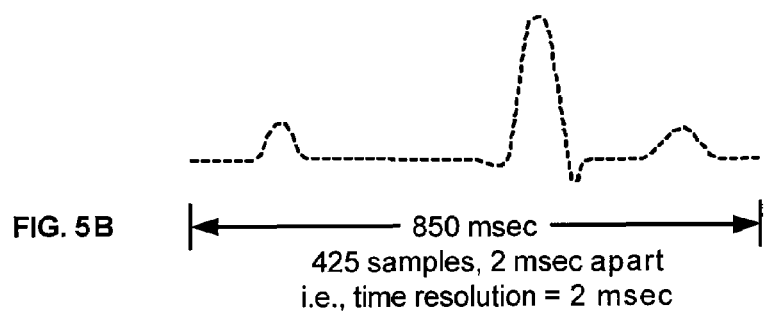
FIG. 5B  |← 850 msec →|
         425 samples, 2 msec apart
         i.e., time resolution = 2 msec
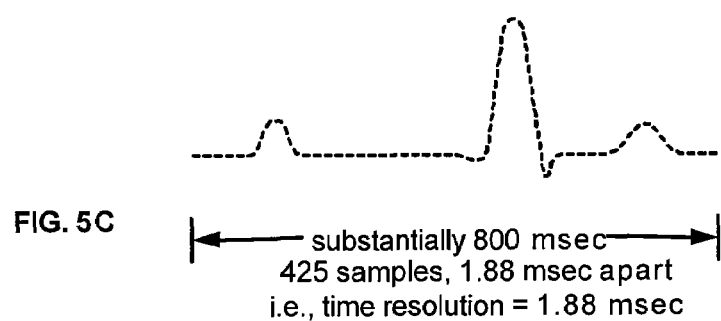
FIG. 5C  |← substantially 800 msec →|
         425 samples, 1.88 msec apart
         i.e., time resolution = 1.88 msec
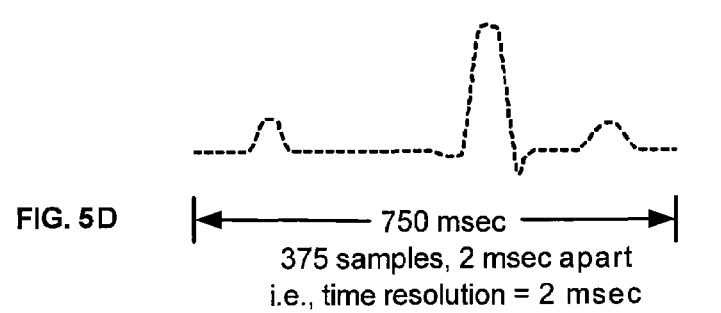
FIG. 5D  |← 750 msec →|
         375 samples, 2 msec apart
         i.e., time resolution = 2 msec
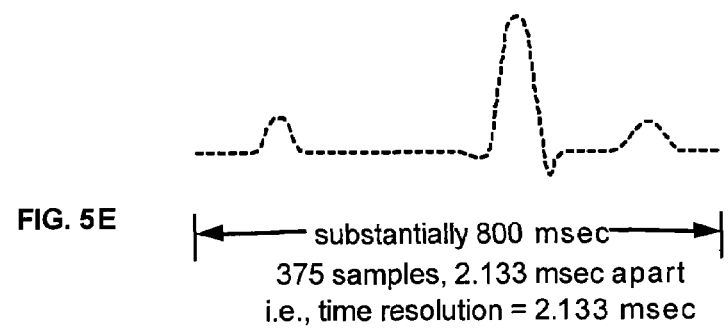
FIG. 5E  |← substantially 800 msec →|
         375 samples, 2.133 msec apart
         i.e., time resolution = 2.133 msec

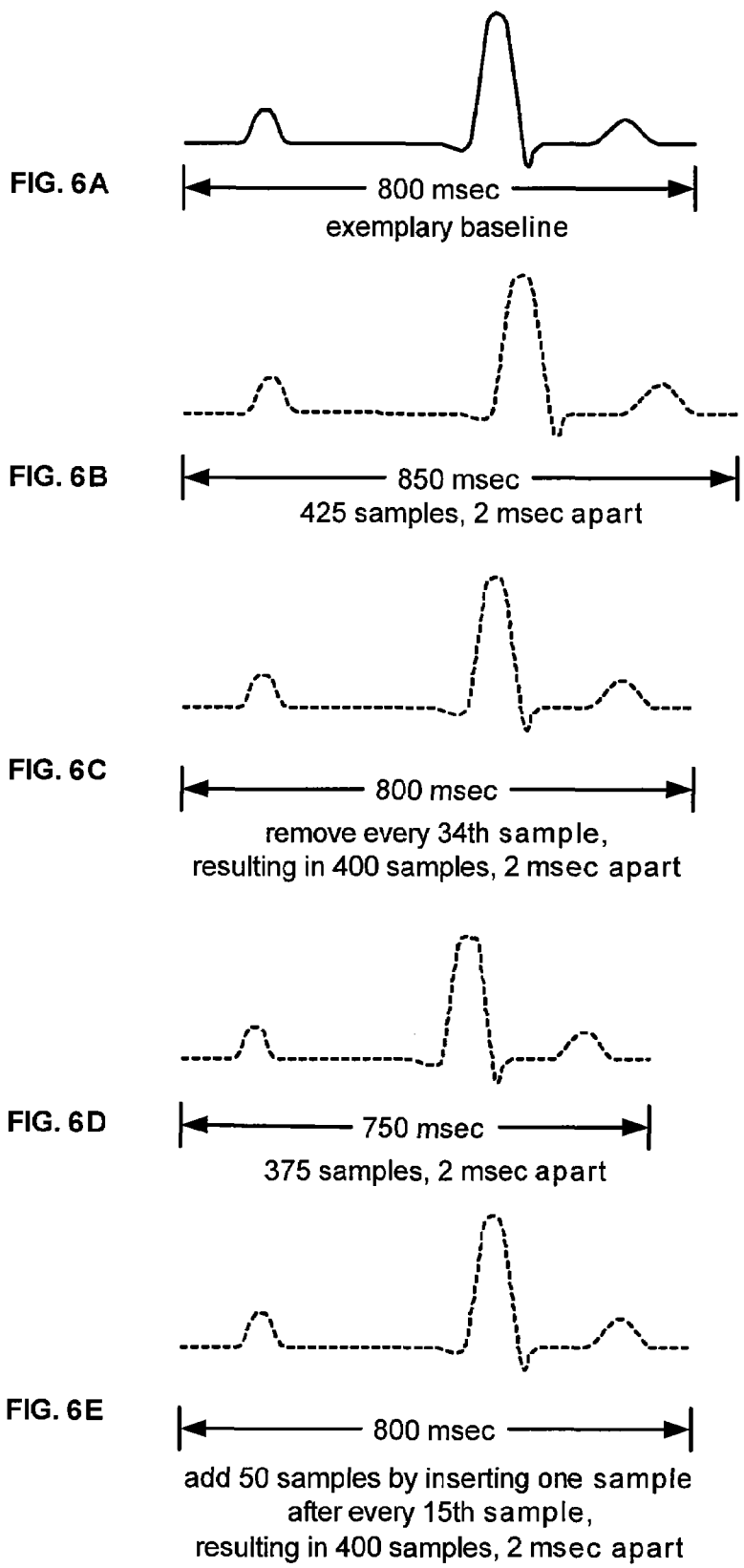

SYSTEMS AND METHODS FOR DETECTING ALTERNANS IN INTRINSIC RHYTHMS TO MONITOR MYOCARDIAL STABILITY

FIELD OF THE INVENTION

The present invention generally relates methods and devices that are capable of monitoring myocardial electrical stability and/or myocardial mechanical stability.

BACKGROUND

Electrical alternans relate to the differences in electrical potential at corresponding points between alternate heartbeats. For example, Twave alternans or alternation is a regular or beat-to-beat variation of the ST-segment or Twave, which repeats itself every beat group (e.g., two beats, three beats or four beats), and has been linked to underlying cardiac electrical instability.

Microvolt Twave alternans (TWA) has been demonstrated in many studies as a strong predictor of mortality, independent of left ventricular ejection fraction (LVEF). Macrovolt Twave alternans (TWA) has been observed prior to VT/VF (3-8 minutes) in patients with acute coronary/LQT syndrome and as such, is considered a precursor to VT/VF. Hence, detection of Twave alternans can be a potent predictor of arrhythmia onset.

Conventional Twave alternans detection methods require or assume very consistent cardiac cycle lengths (e.g., RR intervals), which inherently do not exist in intrinsic sinus rhythms. Rather, there is an intrinsic variability in cardiac cycle lengths during intrinsic sinus rhythms. Such intrinsic variability in cardiac cycle lengths make it difficult to consistently and accurately detect Twave alternans. This is because if the "same" location in Twave is not detected in every heart beat, variation, and even alternation in its amplitude may be misdetected as Twave alternans. Thus, it would be beneficial if Twave alternans, and other types of electrical alternans, could be consistently and accurately detected even when there is variability in cardiac cycle lengths.

Mechanical alternans, also known as mechanical pulse alternans (MPA), relate to the situation where alternating contractions of the heart exhibit alternating values of contraction force or magnitude that cause ejected blood to exhibit similar alternating values of diastolic pressure amplitude. For example, the presence of mechanical alternans can be defined by a consistent alternation in peak left ventricular (LV) pressure, or dP/dt, in successive beats.

The detection of mechanical alternans can be a potent predictor of congestive heart failure caused by global left ventricular dysfunction, and is considered to be a terminal sign in this population. Accordingly, it is believed that it would be useful to provide accurate methods and systems for chronically monitoring for mechanical alternans, and more generally, monitoring myocardial mechanical stability.

As with conventional Twave alternans detection methods, conventional mechanical alternans detection methods require or assume very consistent cycle lengths, which inherently do not exist in intrinsic cardiac rhythms. However, intrinsic variability in cycle lengths makes it difficult to consistently and accurately detect mechanical alternans. Accordingly, it would be beneficial if mechanical alternans could be consistently and accurately detected even when there is variability in cardiac cycle lengths.

BRIEF SUMMARY OF THE INVENTION

Embodiments of the present invention relate to implantable systems, and methods for use therewith, for monitoring myocardial electrical stability and/or myocardial mechanical stability.

Specific methods of the present invention obtain sample data that is representative of functioning of a patient's heart for a plurality of consecutive beats, wherein each beat has a corresponding cycle length that may differ from cycle lengths of other beats. Such sample data is adjusted so that cycle lengths of consecutive beats represented in the adjusted sample data are substantially equal. Myocardial stability is then monitored based on the adjusted sample data. Where the obtained sample data is representative of electrical functioning of the patient's heart, myocardial electrical stability can be monitored, e.g., by monitoring for electrical alternations. Where the obtained sample data is representative of mechanical functioning of the patient's heart, myocardial mechanical stability can be monitored, e.g., by monitoring for mechanical alternans.

In accordance with specific embodiments, a baseline cycle length is specified, and cycle lengths that are shorter than the baseline are increased, and cycle lengths that are longer than the baseline are decreased. Cycle lengths equal to the baseline need not be adjusted. Such a baseline can be, e.g., predetermined, or a mean of a plurality of cycle lengths represented by the sample data, or by previous sample data. It is also possible that the sample data is upsampled prior to the sample data being adjusted, and then downsampled after the adjusting, to thereby produce the adjusted sample data.

In accordance with certain embodiments, to increase a cycle length corresponding to a beat that is shorter than the baseline cycle length, the time resolution of the sample data for that beat can be increased. Conversely, to decrease a cycle length corresponding to a beat that is longer than the baseline cycle length, the time resolution of the sample data for that beat can be decreased.

In accordance with certain embodiments, to increase a cycle length corresponding to a beat that is shorter than the baseline cycle length, additional sample data can be inserted for that beat. Conversely, to decrease a cycle length corresponding to a beat that is longer than the baseline cycle length, some sample data for that beat can be removed. Preferably, the sample data added to or removed from a beat is substantially evenly distributed throughout the beat so as to minimize changes to the morphology of the signal represented in the sample data. In accordance with specific embodiments, interpolation is used to determine the values of sample data being added to increase cycle lengths.

This description is not intended to be a complete description of, or limit the scope of, the invention. Other features, aspects, and objects of the invention can be obtained from a review of the specification, the figures, and the claims.

BRIEF DESCRIPTION OF THE DRAWINGS

FIG. 5A illustrates an exemplary baseline waveform.

FIG. 5B illustrates example sample data for a portion of a signal having a cycle length greater than that of the baseline shown in FIG. 5A.

FIG. 5C is used to describe how the time resolution of the sample data of FIG. 5B can be adjusted to have a cycle length substantially equal to the cycle length of the baseline waveform shown in FIG. 5A, in accordance with an embodiment of the present invention.

FIG. 5D illustrates example sample data for a portion of a signal having a cycle length greater than that of the baseline shown in FIG. 5A.

FIG. 5E is used to describe how the time resolution of the sample data of FIG. 5D can be adjusted to have a cycle length substantially equal to the cycle length of the baseline waveform shown in FIG. 5A, in accordance with an embodiment of the present invention.

FIG. 6A illustrates an exemplary baseline waveform.

FIG. 6B illustrates example sample data for a portion of a signal having a cycle length greater than that of the baseline shown in FIG. 6A.

FIG. 6C is used to describe how the some of the sample data of FIG. 6B can be removed to achieve a cycle length substantially equal to the cycle length of the baseline waveform shown in FIG. 6A, in accordance with an embodiment of the present invention.

FIG. 6D illustrates example sample data for a portion of a signal having a cycle length greater than that of the baseline shown in FIG. 6A.

FIG. 6E is used to describe how additional sample data can be inserted into the sample data of FIG. 6D to achieve a cycle length substantially equal to the cycle length of the baseline waveform shown in FIG. 6A, in accordance with an embodiment of the present invention.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
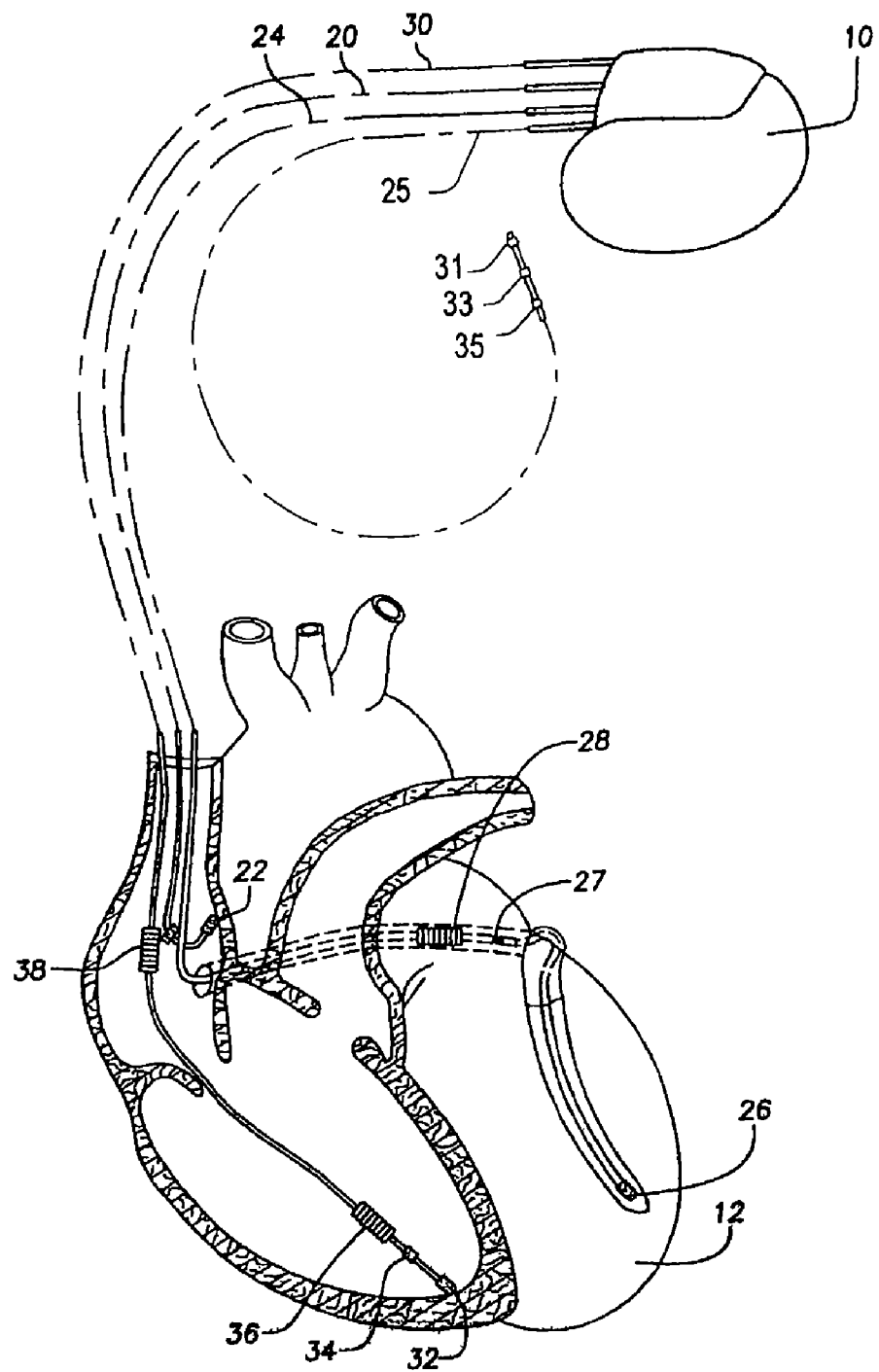
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
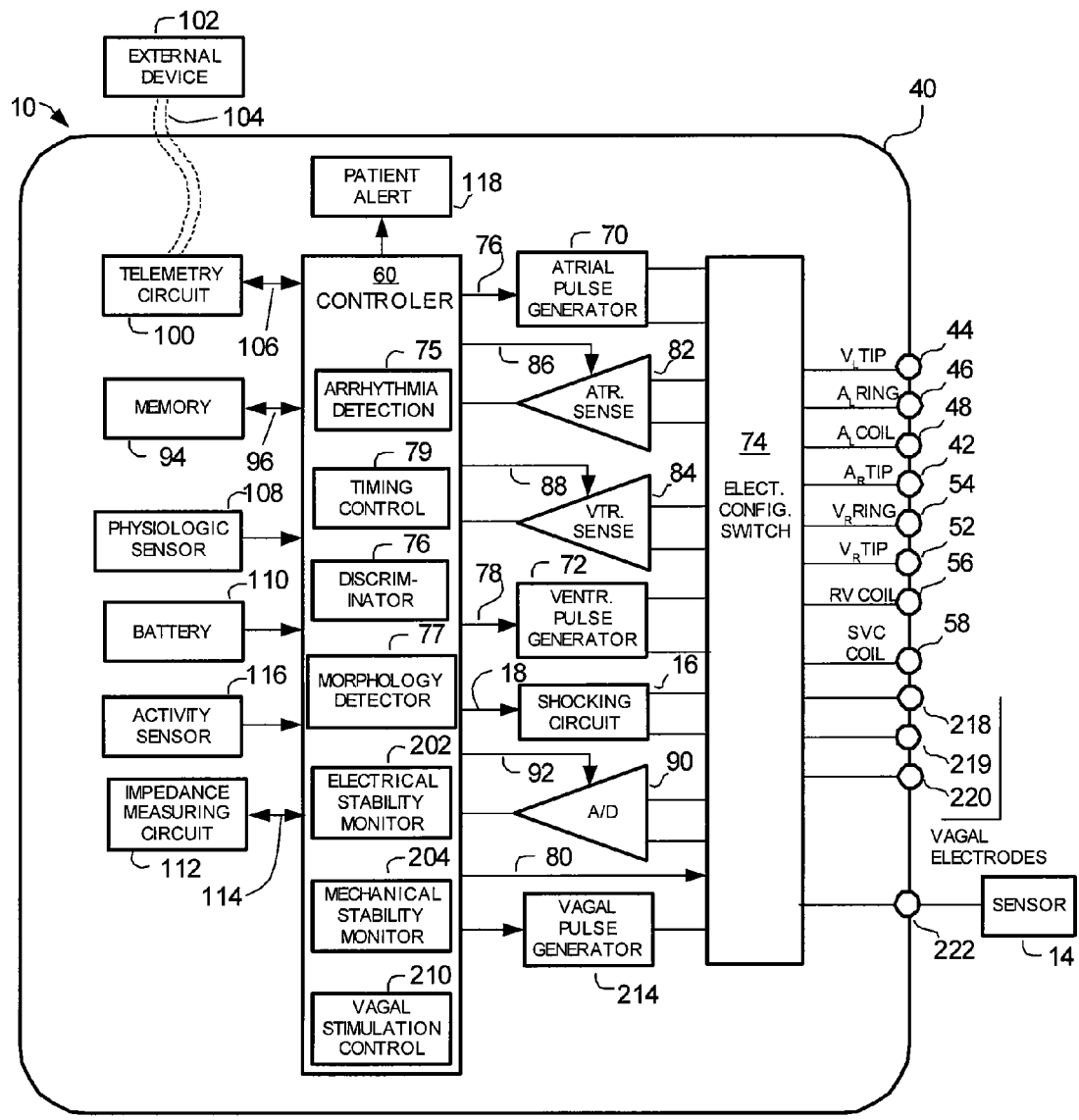
FIG. 2 is a functional block diagram of an exemplary ICD that can provide cardioversion, defibrillation, and pacing stimulation in four chambers of a heart, and monitor myocardial electrical and mechanical stability, in accordance with embodiments of the present invention.

Before describing the invention in detail, it is helpful to describe an example environment in which embodiments of the invention may be implemented. The present invention is particularly useful in the environment of an implantable cardiac device that can monitor electrical and mechanical activity of a heart and deliver appropriate therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multichamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

One of the above described leads (or a further lead) can also connect a further sensor (not specifically shown in FIG. 1, but shown as sensor 14 in FIG. 2) to the ICD 10, where the further sensor 14 is capable of measuring the mechanical functioning of the heart, or a surrogate thereof. In one embodiment, the sensor 14 is a pressure transducer that obtains measures of ventricular pressure. In another embodiment, the sensor 14 is an accelerometer that obtains measures of contraction strength. In a further embodiment, the sensor 14 is a blood flow transducer that obtains measures of blood flow rate. In still another embodiment, the sensor 14 is an acoustic transducer that obtains measures of heart sounds. Such an acoustic transducer can be, e.g., a microphone or an accelerometer that responds to acoustic vibrations transmitted through body fluids, to thereby detect alternating loud and soft sounds. In a further embodiment, the sensor 14 is an impedance measuring circuit having voltage sense electrodes to measure volumetric alternans, which is a surrogate of mechanical alternans. In still another embodiment, the sensor 14 is a photoplethysmography (PPG) sensor that measure pulse pressure. In a further embodiment, the sensor is a venous oxygen saturation (SVO2) sensor that measures venous oxygen saturation levels, which are believed to be indicative of mechanical functioning of the heart. These are just some examples of sensors that are capable of measuring the mechanical functioning of the heart, or a surrogate thereof. Other types of sensors capable of measuring the mechanical functioning of the heart, or a surrogate thereof, are also within the scope of the present invention.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts. Additionally, where the sensor 14 is connected to the ICD by its own lead, the connector can include a terminal 222, which is configured for connecting the sensor 14 to the ICD. It is also possible that the sensor 14 is integrated with the housing 40, and thus does not need to be connected via a terminal.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrioventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting electrical alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

Still referring to FIG. 2, in accordance with certain embodiments of the present invention, microcontroller 60 includes myocardial electrical stability monitor 202, which as described in more detail below, can detect the presence of electrical alternans, such as T-wave alternans, as well as determine levels of electrical alternation. The monitor 202 can be implemented within the microcontroller 60, as shown in FIG. 2. Thus, monitor 202 can be implemented by software, firmware, or combinations thereof. It is also possible that all, or portions, of monitor 202 can be implemented using hardware. Further, it is possible that all, or portions, of monitor 202 be implemented external to the microcontroller 60.

In an embodiment, monitor 202 triggers data acquisition circuit 90 and timing control circuit 79 to record IEGM signal information. Monitor 202 can measure intrinsic and evoked T-wave metrics, such as T-wave amplitude, T-wave amplitude, T-wave width, T-wave slope, T-wave area, T-wave morphology, QT interval, etc. in the IEGM signal generated by the sensing circuits of the data acquisition system 90. Monitor 202 can also trigger the implantable device 10 to respond appropriately when T-wave alternans are detected, as will be explained in more detail below. Additionally, in conjunction with a telemetry circuit 100, monitor 202 can be configured to deliver status information, relating to the patient's T-wave alternans, to an external device 102 through an established communication link 104. Monitor 202 may also trigger a patient or physician alert in response to detecting T-wave alternans. For example, a patient alert 118, which produces a vibratory or auditory alert, may be triggered by the monitor 202.

In accordance with certain embodiments of the present invention, the microcontroller 60 also includes a myocardial mechanical stability monitor 204, which as described in more detail below, can monitor myocardial mechanical stability, e.g., by detecting the presence of mechanical alternans. The myocardial mechanical stability monitor 204 can be implemented within the microcontroller 60. Thus, myocardial mechanical stability monitor 204 can be implemented by software, firmware, or combinations thereof. It is also possible that all, or portions, of the myocardial mechanical stability monitor 204 can be implemented using hardware. Further, it is possible that all, or portions, of the myocardial mechanical stability monitor 204 be implemented external to the microcontroller 60.

In an embodiment, the myocardial mechanical stability monitor 204 triggers data acquisition circuit 90 and timing control circuit 79 to acquire a signal that is indicative of mechanical functioning of a patient's heart. Such a signal can be representative of an actual measure of mechanical functioning, or representative of a surrogate of mechanical functions. For an example, such a signal, if obtained from a pressure transducer within a ventricle, can be representative of ventricular pressure. In another embodiment, the signal is representative of contraction strength, which can be obtained from an accelerometer. In a further embodiment, the signal is representative of blood flow rate, which can be obtained from a blood flow transducer. In another embodiment, the signal is representative of heart rate sounds, which can be obtained from a microphone or an accelerometer that responds to acoustic vibrations transmitted through body fluids. In still another embodiment, the signal can representative of blood volume, which can be obtained using an impedance measuring circuit. In still another embodiment, the signal can be representative of pulse pressure, which can be obtained using a photo-plethysmography sensor. In still another embodiment, the signal can be representative of venous oxygen saturation (SVO2). Each of the above are exemplary sensors that can be used to acquire a signal that is representative of mechanical functioning of a patient's heart, or a surrogate thereof. One of ordinary skill in the art, based on the disclosure herein, would understand that use of other types of sensors are also within the scope of the present invention.

Each of the above described signals are cyclical because they are indicative of the mechanical functioning of the heart, with each cycle of the signal corresponding to a beat of the patient's heart. The myocardial mechanical stability monitor 204 can measure metrics of each cycle of the signal (i.e., metrics of each beat), to thereby determine whether there is an alternation in such metrics. Examples of such metrics include, but are not limited to, amplitude, width, area, and morphology. Depending on the signal being analyzed, the metrics can also be of specific portions or markers within the signal. The myocardial mechanical stability monitor 204 can also trigger the implantable device 10 to respond appropriately when mechanical alternans are detected, as will be explained in more detail below. Additionally, in conjunction with the telemetry circuit 100, the myocardial mechanical stability monitor 204 can be configured to deliver status information, relating to the patient's myocardial mechanical stability, to the external device 102 through an established communication link 104. The myocardial mechanical stability monitor 204 may also trigger a patient or physician alert in response to detecting mechanical alternans. For example, a patient alert 118, which produces a vibratory or auditory alert, may be triggered by the myocardial mechanical stability monitor 204.

Adjusting Cycle Lengths

In accordance with specific embodiments of the present invention, the monitor 202 monitors for electrical alternans in order, e.g., to predict mortality, predict an impending arrhythmia, or the like. Additionally, or alternatively, the monitor 204 monitors for mechanical alternans. As mentioned above, the intrinsic variability cardiac cycle lengths makes it difficult for conventional electrical and mechanical alternans detection methods to consistently and accurately detect alternans. Embodiments of the present invention, as will now be described, enable alternans to be consistently and accurately detected even when there is variability in cardiac cycle lengths. More generally, embodiments of the present invention, as will be appreciated from the high level flow diagram of FIG. 3, can be used when monitoring the electrical stability and/or mechanical stability of a patient.

Figure 3:
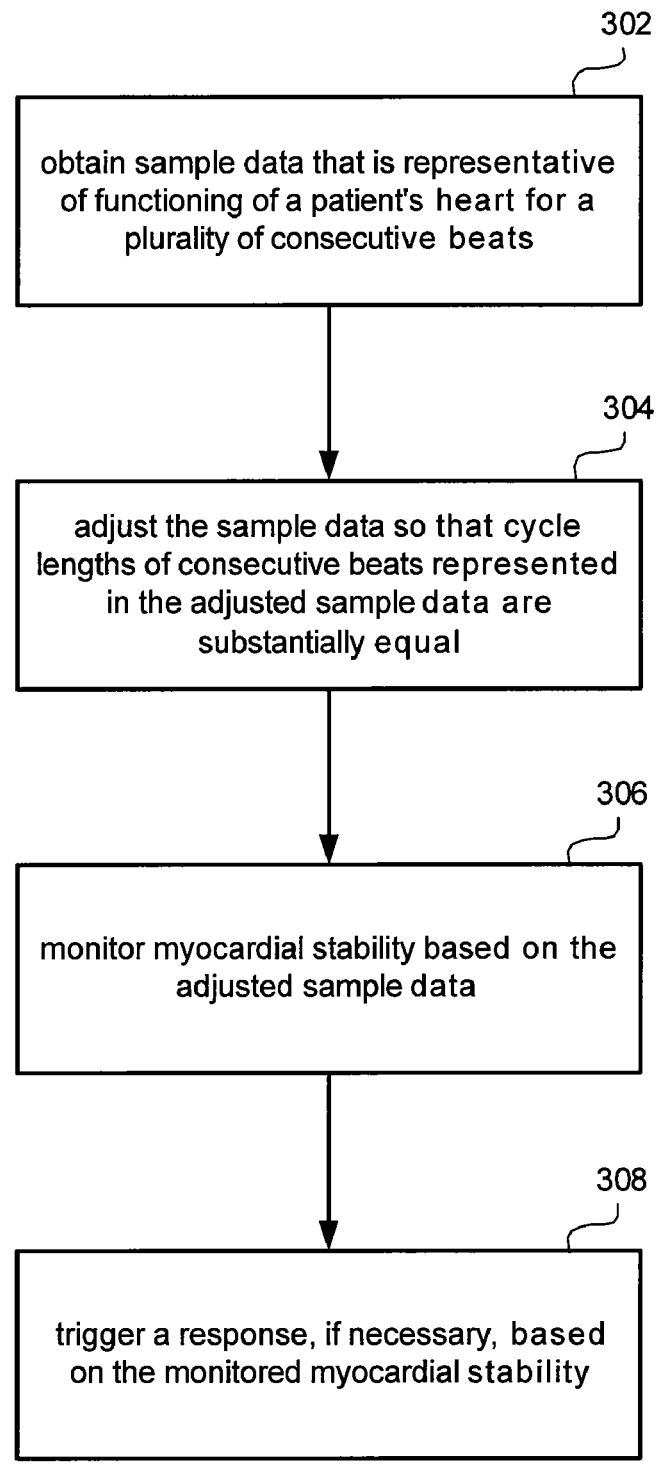
FIG. 3 is a high level flow diagram that is useful for summarizing specific embodiments of the present invention where cycle lengths are adjusted to improve the monitoring of myocardial electrical and/or mechanical stability.

FIG. 3 is a high level flow diagram that is useful for summarizing specific embodiments of the present invention where cycle lengths are adjusted to improve the monitoring of myocardial stability. Referring to FIG. 3, step 302 includes obtaining sample data that is representative of functioning of a patient's heart for a plurality of consecutive beats, wherein each beat has a corresponding cycle length that may differ from cycle lengths of other beats.

In certain embodiments, the sample data is representative of electrical functioning of the patient's heart. In such embodiments, the sample data can include samples of an EGM signal obtained from the implanted electrodes discussed above with reference to FIGS. 1 and 2.

In other embodiments the sample data is representative of mechanical functioning of the patient's heart. In such embodiments, the sample data can include samples of, e.g., a signal representative of ventricular pressure obtained using a pressure transducer within a ventricle, a signal representative of contraction strength obtained from an accelerometer, a signal is representative of blood flow rate obtained from a blood flow transducer, a signal is representative of heart rate sounds obtained from a microphone or an accelerometer that responds to acoustic vibrations transmitted through body fluids, a signal representative of blood volume obtained using an impedance measuring circuit, a signal representative of pulse pressure obtained using a photo-plethysmography sensor, or a signal can be representative of venous oxygen saturation (SVO2) obtained from a pulse oximetry sensor.

Figure 4:
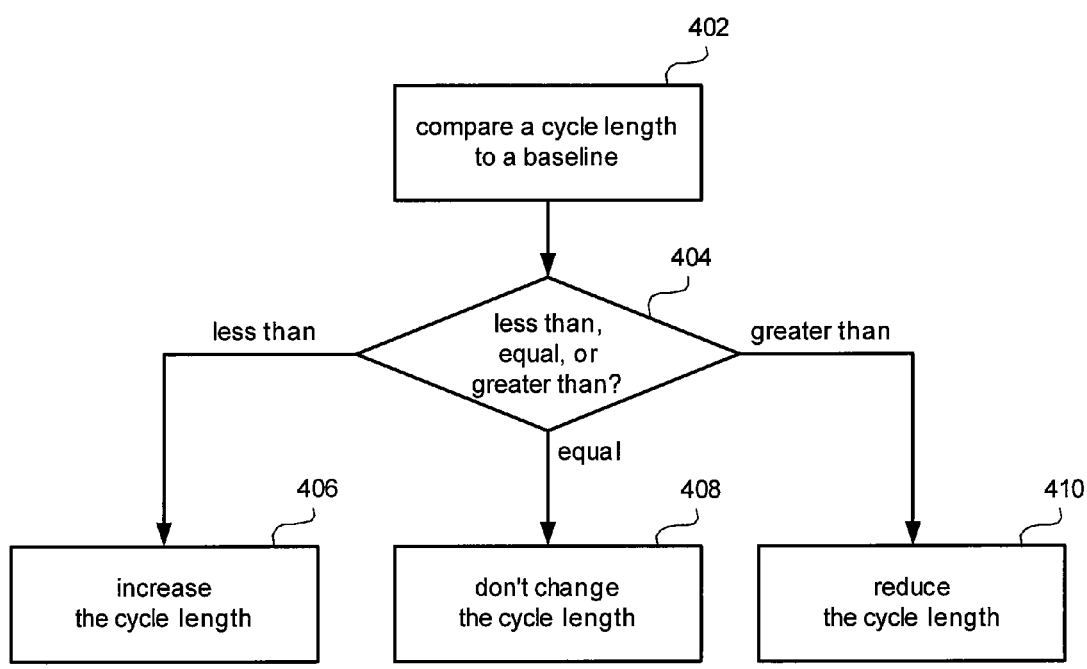
FIG. 4 is a flow diagram that is useful for describing additional details of step 304 from FIG. 3, according to specific embodiments of the present invention.

At step 304, the sample data is adjusted so that cycle lengths of consecutive beats represented in the adjusted sample data are substantially equal. In accordance with specific embodiments, step 304 includes increasing cycle lengths that are shorter than a baseline cycle length, and decreasing cycle lengths that are longer than the baseline cycle length. Cycle lengths already equal to the baseline need not be adjusted. The above description of step 304 is summarized in steps 402-410 in the flow diagram of FIG. 4.

The baseline can be, e.g., a predetermined cycle length, the mean (average) or median of previous cycle lengths, or the mean (average) or median of the cycle lengths represented in the sample data. One of ordinary skill in the art would appreciate that there are other ways of determining or defining a baseline that are within the scope of the present invention.

In accordance with specific embodiments, a cycle length corresponding to a beat that is shorter than the baseline cycle length is increased by increasing the time resolution of the sample data for that beat. Conversely, a cycle length corresponding to a beat that is longer than the baseline cycle length is decreased by decreasing the time resolution of the sample data for that beat. The term "time resolution", as used herein, refers to the time between sample data points. For example, assume that sample data is obtained by sampling a signal at 500 samples per second. This would result in sample data having a time resolution of $2 \times 10^{-3}$ seconds ($1/500 = 2 \times 10^{-3}$), i.e., 2 msec. Now also assume that a baseline cycle length is 800 msec (corresponding to a baseline heart rate of 75 beats/minute), as shown in FIG. 5A. Also assume that the cycle length corresponding to a beat of the sample data is 850 msec, as shown in FIG. 5B. In order to decrease the cycle length of the beat of the sample data from 850 msec to 800 msec, the time resolution of the sample data can be reduced from 2 msec to 1.88 msec, as illustrated in FIG. 5C. For another example, assume the cycle length corresponding to a beat of the sample data is 750 msec, as shown in FIG. 5D. In order to increase the cycle length of the beat of the sample data from 750 msec to 800 msec, the time resolution of the sample data can be increased from 2 msec to 2.133 msec, as illustrated in FIG. 5E.

In accordance with other embodiments of the present invention, a cycle length corresponding to a beat that is shorter than the baseline cycle length is increased by inserting additional sample data for the beat. Preferably the additional sample data that is inserted is substantially evenly distributed throughout the beat whose cycle length is being increased, so as to maintain the morphology of the portion of the signal represented in the data. Conversely, a cycle length corresponding to a beat that is longer than the baseline cycle length is decreased by removing sample data for that beat. Preferably, the sample data removed for a beat at is substantially evenly distributed throughout the beat whose cycle length is being decreased, again to maintain the morphology of the portion of the signal represented in the data.

For example, again assume that sample data is obtained by sampling a signal at 500 samples per second, and that a baseline cycle length is 800 msec (corresponding to a baseline heart rate of 75 beats/minute), as shown in FIG. 6A. Also assume that the cycle length corresponding to a beat of the sample data is 850 msec, as shown in FIG. 6B. In order to decrease the cycle length of the beat of the sample data from 850 msec to 800 msec, 25 sample data points can be removed. To minimize altering the morphology of the portion of the signal represented by the sample data, every $34^{th}$ sample can be removed, as illustrated in FIG. 6C. For another example, assume the cycle length corresponding to a beat of the sample data is 750 msec, as shown in FIG. 6D. In order to increase the cycle length of the beat of the sample data from 750 msec to 800 msec, 50 additional samples can be inserted into the sample data. To minimize altering the morphology of the portion of the signal represented by the sample data, a single sample can be inserted after every 15 samples of the sample data, as illustrated in FIG. 6E. Values of the sample data being added can be determined using interpolation. A simple interpolation algorithm can involve averaging the samples on either side of where the sample is being inserted. It is also possible that the added sample data is simply made equal to the sample which it is to precede or proceed after being inserted. In another embodiment, when a sample is removed, one of the samples next to the removed sample is replaced with an average of the removed sample and the sample being replaced. Alternative interpolation algorithms may also be used, if desired.

Cycle lengths can also be adjusted by both adjusting time resolution and adding or removing samples. It is also within the scope of the present invention that alternative methods be used to adjust cycle lengths such that cycle lengths of consecutive beats represented in the adjusted sample data are substantially equal. It is also within the scope of the present invention that up-sampling and down-sampling can be used. For example, if a signal were originally sampled at 500 Hz, it could be upsampled to 1000 Hz, cycle lengths extended or compressed to match a baseline (in any of the manners discussed above), and then down-sampled again to 500 Hz. Such up-sampling and down-sampling is meant to be encompassed within step 304.

Referring back to FIG. 3, once the cycle lengths of consecutive beats represented in the sample data are adjusted to be substantially equal, myocardial stability can be monitored based on the adjusted sample data, as indicated at step 306. Further, as indicated at step 308, an appropriate response can be triggered based on the monitored myocardial stability.

Where the sample data obtained at step 302 is representative of the electrical functioning of the patient's heart, then myocardial electrical stability can be monitored at step 306 based on the adjusted sample data. This can include determining whether electrical alternans (e.g., T-wave alternans) are present and/or determining a level of electrical alternation. For example, this can include determining metrics of T-waves of the plurality of consecutive beats, based on the adjusted sample data, and determining whether T-wave alternans are present based on the determined T-wave metrics. Exemplary methods for determining whether electrical alternans are present are discussed below.

In accordance with certain embodiments, a window of N beats (where N is preferably a multiple of the number of cardiac cycles in one respiration cycle) of a signal is constantly monitored to produce a stable value of the average cycle length (e.g., average RR interval), which can be used as the baseline cycle length. To produce a stable value for the baseline cardiac cycle length, the window is preferably long enough so that the baseline cycle length is not affected by transient fluctuations such as that caused by single ectopic beats. Cardiac cycle lengths can also be monitored in real-time. If the current cardiac cycle length is different from the baseline cycle length, the EGM of that beat is processed and is either shrunk or stretched to match the same length as defined by the baseline cycle length. If the current cardiac cycle length matches the baseline, it is not processed and used as is. The algorithm will then analyze a window of M beats of the adjusted EGM to monitor for electrical alternans, e.g., Twave alternans. For example, first the location of Twaves can be marked using a predefined criterion and their amplitudes are measured. Then the set of M Twave amplitudes can be analyzed to detect a significant and consistent difference between odd and even beats. This can be accomplished using a variety of time domain or frequency domain techniques. If the algorithm finds that Twave alternans are present, an alert can be activated, which may in turn notify the patient and/or a physician, or turn on a preventative therapy (such as vagal stimulation) or preventative pacing (anti-tachycardia pacing, non-resonant pacing, etc.).

Where the sample data obtained at step 302 is representative of mechanical functioning of the patient's heart, then myocardial mechanical stability can be monitored at step 306 based on the adjusted sample data. This can include determining whether mechanical alternans (also known as pulses alternans) are present and/or determining a level of mechanical alternation. Exemplary methods for determining whether mechanical alternans are present are discussed below.

Responses

One or more response can be triggered at step 308 (of FIG. 3). In accordance with an embodiment of the present invention, information related to electrical and/or mechanical alternans can be stored. This can include, for example, storing amplitude, slope, timing, and/or duration information relating to the alternans. Such information can be continually, or from time to time, automatically uploaded to an external device (e.g., 102). Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

As mentioned above, electrical alternans are a known predictor of arrhythmic events such as tachyarrhythmias, and mechanical alternans are a known predictor of worsening heart failure. Accordingly, in an embodiment, a patient is alerted (e.g., using alert 118) when electrical and/or mechanical alternans are detected. Such an alert could be a vibratory or auditory alert that originates from within the implantable device 10. Alternatively, the implantable device 10 may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible the a tachyarrhythmias may be avoided, or if it does occur, the patient will be less dangerous to themselves and others if the patient is resting when the tachyarrhythmias occurs (as opposed, e.g., to driving a car). Additionally or alternatively, the patient can be instructed to take medication when alerted. In still another embodiment, a physician or other person (e.g., a caregiver, guardian or relative of the patient) is alerted whenever the presence of electrical and/or mechanical alternans is detected.

In further embodiments, therapy can be triggered in response to detecting the presence of electrical and/or mechanical alternans. The type of therapy can be specific to the types of alternans, and also to the magnitude of alternans. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate drug therapy. In still another embodiment, the implanted device, if appropriately equipped, can deliver appropriate pacing therapy. In still another embodiment, the implantable device, if cable of delivering shock therapy, can begin to charge its capacitors in case the patient goes into ventricular fibrillation and needs shock therapy. These are just a few examples of the types of responses that can be performed. One of ordinary skill in the art would understand from the above description that other response are also possible, while still being within the spirit and scope of the present invention.

In further embodiments, changes in myocardial electrical and/or mechanical stability are tracked, as described above, and one or more of the above described responses occur if the instability of the myocardium exceeds a corresponding threshold, or stability of the myocardium falls below a corresponding threshold.

Monitoring Myocardial Stability

As explained above, embodiments of the present invention generally relate to adjusting sample data representative of the functioning of a patient's heart for a plurality of consecutive beats, so that the cycle lengths are substantially equal, to thereby enable monitoring of myocardial stability to be more accurate. As also explained above, the myocardial stability that is monitored can be electrical and/or mechanical stability.

For example, to monitor myocardial electrical stability, T-wave metrics can be measured to determined whether alternations in T-waves exist, and to what extent. Below are some example of how T-wave alternans can be detected. However, it is noted that embodiments of the present invention should not be limited to the specific techniques described.

The term T-wave as used herein may refer to a portion of the ventricular QRS-T-wave complex that includes the T-wave and/or the QRS-T segment. The alternating feature of Twave alternans can be detected by examination, for example, of the QT interval, T-wave width, T-wave amplitude, morphology, etc. Whatever the designated portion of the intracardiac electrogram, electrical alternans refers to an alternating pattern of the wave that can be designated "ABABAB . . . " where A represents every other cycle and B represents every other alternate cycle. Such a pattern is often referred to as a two beat alternans pattern, or simply an AB pattern. Electrical alternans may also refer to an alternating pattern of the wave that can be designated "ABCABC . . . ", or an alternating pattern of the wave that can be designated "ABCDABCD . . . ". The "ABCABC . . . " pattern is a three beat alternans pattern, which can be simply referred to as an ABC pattern, and the "ABCDABCD . . . " pattern is a four beat alternans pattern, which can be referred to as an ABCD pattern.

One way to detect the presence of an AB alternans pattern is to measure T-wave metrics for a plurality of consecutive beats represented in the adjusted sample data resulting from step 304, and then line up all the T-wave metrics of odd beats, and line up all the T-wave metrics of even beats. Ensemble averaging (or some other averaging) can then be performed to produce one or more average "odd" T-wave metric and one or more average "even" T-wave metric. A magnitude of alternation can then be determined by determining a difference between an average "odd" T-wave metric and a corresponding average "even" T-wave metric. This difference (i.e., magnitude of alternation) can be compared to a threshold to determine if T-wave alternans are present. If the difference is less than the threshold, then it can be determined that T-wave alternans are not present. If the difference (i.e., the magnitude of alternation) is greater than the threshold, then it can be determined that the T-wave alternans are present. It is also possible to have multiple thresholds such that in addition to determining whether T-wave alternans are present, changes in magnitudes of alternations can be determined. This can be used, e.g., to determine a degree of the T-wave alternans, which are indicative of myocardial electrical stability. This can also be used for tracking the progression of a disease that influences the electrical stability of the myocardium. Additionally, a degree of the T-wave alternans (or more generally, magnitudes of alternation) can be used as an index of the level of risk for an impending ventricular arrhythmia. This type of algorithm can also be modified to look for other (e.g., three of four beat) alternans patterns.

Alternatively, the variation in T-wave amplitude of successive "odd" T-waves and "even" T-waves can be measured in a sliding window of the adjusted sample data resulting from step 304. The amount of T-wave variation between the odd and even T-waves can be determined. A third measure that determines the statistical significance of the difference in T-wave variations as compared to a baseline can be used to determine the presence, degree, or absence of T-wave alternans, and thus, the electrical stability of the myocardium.

Another option would be to determine, for each pair of odd/even beats represented in the adjusted sample data resulting from step 304, the difference between T-wave amplitudes of the odd and even beats. Assuming such differences (which are examples of magnitudes of alternation) are determined for each of 50 separate pairs of beats, then the differences of the 50 pairs can be averaged to produce an average difference, and the presence of T-wave alternans can then be determined from the average difference.

As mentioned above, not all alternans patterns are two beat patterns. Rather, there can be three beat, four beat, etc. alternans patterns. For example, a four beat alternans (ABCD) pattern can be searched for in the following manner. Assume that 200 consecutive beats are divided into 50 separate 4 beat sets. For each 4 beat set, there can be a determination of the difference between T-wave amplitudes of the 1st and 2nd beats, the 2nd and 3rd beats, and the 3rd and 4th beats, resulting in three differences for each 4 beat set (i.e., a first difference between the metrics for 1st and 2nd beats, a second difference between the metrics for the 2nd and 3rd beats, and a third difference between the metrics for the 3rd and 4th beats). Assuming such differences (which are examples of magnitudes of alternation) are determined for each of 50 separate 4 beat sets, then the first difference of each of the 50 sets can be averaged to produce an average first difference, the second difference of each of the 50 sets can be averaged to produce an average second difference, and the third difference of each of the 50 sets can be average to produce an average third difference. The presence of T-wave alternans can then be determined from the average first difference, the average second difference and the average third difference.

Further algorithms rely of frequency domain analysis for detecting electrical alternans. Such algorithms can be improved by adjusting the sample data so that the cycle lengths represented in the data are substantially equal, prior to converting the sample data to the frequency domain.

Alternative systems and methods for detecting electrical alternans, and more generally, monitoring myocardial electrical stability, are provided in the following commonly assigned applications, which are both incorporated herein by reference: U.S. patent application Ser. No. 11/354,699, entitled "Time Domain Monitoring of Myocardial Electrical Stability,", and U.S. patent application Ser. No. 11/354,732, entitled "Frequency Domain Monitoring of Myocardial Electrical Stability,", both of which were filed Feb. 14, 2006.

These are just a few examples of the ways in which the presence of electrical alternans can be detected, or more generally, that myocardial electrical stability can be monitored, at step 306. One of ordinary skill in the art will appreciate that many other different techniques can be used, while still being within the spirit and scope of the present invention.

Methods for detecting mechanical alternans in a signal representative of mechanical functioning of a patient's heart are similar to those that are used for detecting electrical alternans in a signal representative of electrical functioning of a patient's heart. The difference is the signal being analyzed, and the metric(s) of the signal being measured. Exemplary signals that are indicative of mechanical functioning of a patients heart are provided above. The metric(s) of such signals that can be determined for each of a plurality of consecutive beats can be, e.g., maximum amplitude, peak-to-peak amplitude, width, area, morphology, or the like. Further exemplary systems and methods for detecting mechanical alternans, and more generally, monitoring myocardial mechanical stability, are provided in commonly assigned U.S. patent application Ser. No. 11/421,915, filed Jun. 2, 2006, entitled "Methods and Devices for Monitoring Myocardial Mechanical Stability,", While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for monitoring myocardial stability, comprising:
   (a) obtaining sample data that is representative of functioning of a patient's heart for a plurality of consecutive beats, wherein each beat has a corresponding cycle length that may differ from cycle lengths of other beats;
   (b) adjusting the sample data so that cycle lengths of consecutive beats represented in the adjusted sample data are substantially equal; and
   (c) monitoring myocardial stability based on the adjusted sample data.

2. The method of claim 1, wherein the sample data is upsampled prior to the adjusting, and then downsampled after the adjusting, to thereby produce the adjusted sample data.

3. In an implantable system, a method for monitoring myocardial stability, comprising:
   (a) obtaining sample data that is representative of functioning of a patient's heart for a plurality of consecutive beats, wherein each beat has a corresponding cycle length that may differ from cycle lengths of other beats;
   (b) adjusting the sample data so that cycle lengths of consecutive beats represented in the adjusted sample data are substantially equal wherein adjusting includes:
      (b.1) increasing cycle lengths that are shorter than a baseline cycle length; and
      (b.2) decreasing cycle lengths that are longer than the baseline cycle length; and
   (c) monitoring myocardial stability based on the adjusted sample data.

4. The method of claim 3, further comprising determining a mean cycle length of the beats represented by the sample data or by previous sample data, and using the mean cycle length as the baseline cycle length.

5. The method of claim 3, wherein:
   step (b.1) comprises increasing a cycle length corresponding to a beat that is shorter than the baseline cycle length by increasing the time resolution of the sample data for said beat; and
   step (b.2) comprises decreasing a cycle length corresponding to a beat that is longer than the baseline cycle length by decreasing the time resolution of the sample data for said beat.

6. The method of claim 3, wherein:
   step (b.1) comprises increasing a cycle length corresponding to a beat that is shorter than the baseline cycle length by inserting additional sample data for said beat; and
   step (b.2) comprises decreasing a cycle length corresponding to a beat that is longer than the baseline cycle length by removing sample data for said beat.

7. The method of claim 6, wherein:
   the sample data added for a beat at step (b.1) is substantially evenly distributed throughout said beat whose cycle length is being increased; and
   the sample data removed for a beat at step (b.2) is substantially evenly distributed throughout said beat whose cycle length is being decreased.

8. The method of claim 7, further comprising using interpolation to determine the sample data that is being added at step (b.1).

9. The method of claim 1, wherein:
   the sample data obtained at step (a) in representative of electrical functioning of the patient's heart; and
   step (c) comprises monitoring myocardial electrical stability based on the adjusted sample data.

10. The method of claim 9, wherein step (c) includes:
    (c.1) determining metrics of T-waves of the plurality of consecutive beats, based on the adjusted sample data; and (c.2) determining whether T-wave alternans are present based on the determined T-wave metrics.

11. The method of claim 1, wherein:
the sample data obtained at step (a) in representative of mechanical functioning of the patient's heart; and
step (c) comprises monitoring myocardial mechanical stability based on the adjusted sample data.

12. The method of claim 11, wherein step (c) includes:
(c.1) determining a metric of the sample data for each of the plurality of consecutive beats; and
(c.2) determining whether mechanical alternans are present based on the determined metrics.

13. An implantable system for monitoring myocardial stability, comprising:
means for obtaining sample data that is representative of functioning of a patient's heart for a plurality of consecutive beats, wherein each beat has a corresponding cycle length that may differ from cycle lengths of other beats;
means for adjusting the sample data so that cycle lengths of consecutive beats represented in the adjusted sample data are substantially equal; and
means for monitoring myocardial stability based on the adjusted sample data.

14. The system of claim 13, wherein the means for adjusting upsamples the sample data prior to adjusting the sample data, and then downsamples the sample data after the adjusting, to thereby produce the adjusted sample data.

15. An implantable system for monitoring myocardial stability, comprising:
means for obtaining sample data that is representative of functioning of a patient's heart for a plurality of consecutive beats, wherein each beat has a corresponding cycle length that may differ from cycle lengths of other beats;
means for adjusting the sample data so that cycle lengths of consecutive beats represented in the adjusted sample data are substantially equal; and
means for monitoring myocardial stability based on the adjusted sample data, wherein the means for adjusting increases cycle lengths that are shorter than a baseline cycle length, and decreases cycle lengths that are longer than the baseline cycle length.

16. The system of claim 15, wherein the baseline cycle length comprises a mean cycle length of the beats represented by the sample data or by previous sample data.

17. The system of claim 15, wherein the means for adjusting increases a cycle length corresponding to a beat that is shorter than the baseline cycle length by increasing the time resolution of the sample data for said beat, and decreases a cycle length corresponding to a beat that is longer than the baseline cycle length by decreasing the time resolution of the sample data for said beat.

18. The system of claim 17, wherein the means for adjusting increases a cycle length corresponding to a beat that is shorter than the baseline cycle length by inserting additional sample data for said beat, and decreases a cycle length corresponding to a beat that is longer than the baseline cycle length by removing sample data for said beat.

19. An implantable system for monitoring myocardial stability, comprising:
means for obtaining sample data that is representative of functioning of a patient's heart for a plurality of consecutive beats, wherein each beat has a corresponding cycle length that may differ from cycle lengths of other beats;
means for adjusting the sample data so that cycle lengths of consecutive beats represented in the adjusted sample data are substantially equal; and
means for monitoring myocardial stability based on the adjusted sample data, wherein:
the sample data is representative of electrical functioning of the patient's heart; and
the means for monitoring monitors myocardial electrical stability based on the adjusted sample data.

20. An implantable system for monitoring myocardial stability, comprising:
means for obtaining sample data that is representative of functioning of a patient's heart for a plurality of consecutive beats, wherein each beat has a corresponding cycle length that may differ from cycle lengths of other beats;
means for adjusting the sample data so that cycle lengths of consecutive beats represented in the adjusted sample data are substantially equal; and
means for monitoring myocardial stability based on the adjusted sample data, wherein:
the sample data is representative of mechanical functioning of the patient's heart; and
the means for monitoring monitors myocardial mechanical stability based on the adjusted sample data.

21. In an implantable system, a method for monitoring myocardial stability, comprising:
(a) obtaining a signal that is representative of functioning of a patient's heart for a plurality of consecutive beats, wherein each beat has a corresponding cycle length that may differ from cycle lengths of other beats;
(b) adjusting the signal so that cycle lengths of consecutive beats represented in the signal are substantially equal; and
(c) monitoring myocardial stability based on the adjusted signal.

22. An implantable system for monitoring myocardial stability, comprising:
means for obtaining a signal that is representative of functioning of a patient's heart for a plurality of consecutive beats, wherein each beat has a corresponding cycle length that may differ from cycle lengths of other beats;
means for adjusting the signal so that cycle lengths of consecutive beats represented in the signal are substantially equal; and
means for monitoring myocardial stability based on the adjusted signal.

* * * * *